US006054579A

United States Patent [19]
Harriman

[11] Patent Number: 6,054,579
[45] Date of Patent: Apr. 25, 2000

[54] SYNTHESIS OF SUBSTITUTED LACTAMS

[75] Inventor: Geraldine C. B. Harriman, Charlestown, R.I.

[73] Assignee: LeukoSite, Inc., Cambridge, Mass.

[21] Appl. No.: 09/100,687

[22] Filed: Jun. 19, 1998

Related U.S. Application Data

[60] Provisional application No. 60/050,801, Jun. 26, 1997.

[51] Int. Cl.$^7$ ..................... C07D 207/16; C07D 211/60; C07D 223/10; C07D 225/02
[52] U.S. Cl. .................... 540/200; 540/354; 540/362; 540/451; 540/463; 540/524; 540/527; 540/529; 548/537; 546/245
[58] Field of Search .................... 540/526, 527, 540/529, 524, 451, 463, 200, 354, 362; 548/537; 546/245

[56] References Cited

U.S. PATENT DOCUMENTS 5,190,923  3/1993  Vincent et al. ..................... 514/19

FOREIGN PATENT DOCUMENTS 0 462 884 A1  12/1991  European Pat. Off. .
290 413 A5  5/1991  Germany .

OTHER PUBLICATIONS

Ugi, I., et al., "The Passerini and Ugi Reactions." In *Comprehensive Organic Synthesis, vol. 2*, B.M. Trost, ed., (Pergamon Press, Oxford), p. 1083–1109 (1991).

Ugi, I., et al., "Molecular Libraries in Liquid Phase via UGI–MCR," *Res. Chem. Intermed.*, 22: 625–644 (1996).

Short, K.M., et al., "A Solid–Phase Combinatorial Method for the Synthesis of Novel 5– and 6–Membered Ring Lactams," *Tetrahedron Letters*, 38(3): 359–362 (1997).

Short, K.M., et al., "Exploitation of the Ugi 4CC Reaction: Preparation of Small Molecule Combinatorial Libraries via Solid Phase," *Tetrahedron*, 53(19): 6653–6679 (1997).

Still, C., "Chemical Consequences of Conformation in Macrocyclic Compounds," *Tetrahedron*, 37: 3981–3996 (1981).

Ugi, I., et al., "New Reagents and Methods for the Synthesis of β–Lactams, Peptides and Oligonucleotides," In *Nat. Prod. Chem. III*, A ur Rahman et al., eds. (Springer, Berlin), pp. 107–133 (1988).

Nadin, A., et al., "Seven–Membered Lactams as Constraints for Amide Self–Recognition," *Journal of the American Chemical Society*, 117(38): 9768–9769 (1995).

Harriman, G.C.B., "Synthesis of Small and Medium Sized 2,2–Disubstituted Lactams via the "Intramolecular" Three Component Ugi Reaction ," *Tetrahedron Letters*, 38(32): 5591–5594 (1997).

Abstract for Accession Number 91–311279/43 (from Wold Patent Index Database compiled by Derwent Information Ltd.).

*Primary Examiner*—Mukund J. Shah
*Assistant Examiner*—Bruck Kifle
*Attorney, Agent, or Firm*—Hamilton, Brook, Smith & Reynolds, P.C.

[57] ABSTRACT

The invention relates to an efficient and facile method for the preparation of substituted lactams, as described herein. The method comprises reacting a difunctional component containing an activated carbon, an amine capable of forming an imine with the activated carbon of the difunctional component, and an isocyanide in a nucleophilic polar protic solvent and at a concentration of reactants which facilitates the formation of the substituted lactams. The invention also relates to novel substituted lactams, libraries comprising such lactams, and a method of generating libraries substituted lactams, using the method of the invention.

16 Claims, No Drawings

SYNTHESIS OF SUBSTITUTED LACTAMS

RELATED APPLICATION(S)

This application claims the benefit of U.S. Provisional Application Ser. No. 60/050,801, filed Jun. 26, 1997, the entire teachings of which are incorporated herein by reference.

BACKGROUND OF THE INVENTION

An Ugi reaction, commonly referred to as a four-component condensation (4CC), involves the reaction of a ketone or aldehyde, an isocyanide, a carboxylic acid and an amine. The reaction, which yields a bisamide, is depicted as follows:

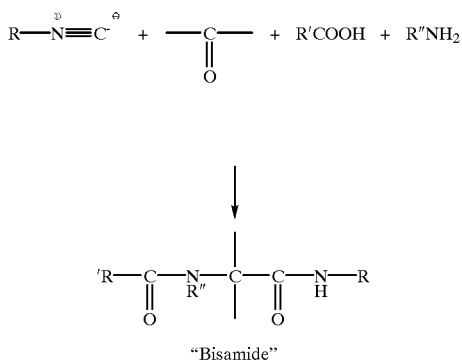

"Bisamide"

This reaction is of particular interest in peptide synthesis where an N-protected amino acid or peptide and/or an isonitrile containing a C-protected carboxyl group would be employed.

SUMMARY OF THE INVENTION

This invention relates to an efficient and facile method for the preparation of substituted lactams having a ring size from about four to about eight or more members. In a preferred embodiment, the substituted lactams have a ring size of either seven or eight. The lactams can be further substituted (by $R^2$) at the two position of the lactam ring, and/or at the amide nitrogen of the ring (by $R^1$), and/or on the remaining carbon atoms of the lactam ring (by $R^3$–$R^6$). The substitution can be a monosubstitution or disubstitution, as appropriate.

One embodiment of the present invention is a method of preparing a lactam represented by the following structural formula:

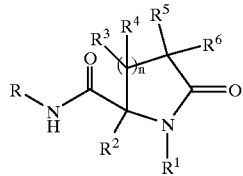

The method comprises reacting a corresponding difunctional component (i.e., a ω-carboxyladehyde or a keto-acid), an amine and isocyanide in a nucleophilic polar protic solvent at a concentration suitable to form the lactam. R, $R^1$, $R^2$, $R^3$, $R^4$, $R^5$, $R^6$ and n can be selected according to the product(s) desired.

The present invention further relates to novel compounds and libraries comprising compounds represented by the above formula.

The present invention has many advantages. For example, the method can be used to prepare lactams, including novel lactams of the present invention, easily and economically. Using the method of the present invention, lactams which are substituted at various and, optionally, multiple positions of the lactam ring, as described above, and having from about a four to about an eight membered ring can be synthesized more economically, with less difficulty and in higher yields than was previously possible. Moreover, the method of the invention provides a single vessel reaction useful in the preparation of 2-acylamino substituted lactams having seven or eight membered rings in particular, where none previously existed.

DETAILED DESCRIPTION OF THE INVENTION

The features and other details of the invention will now be more particularly described and pointed out below as well as in the claims. It will be understood that the particular embodiments of the invention are shown by way of illustration and not as limitations of the invention. The principal features of this invention can be employed in various embodiments without departing from the scope of the invention.

According to the present invention an efficient and facile synthesis of substituted lactams is achieved when the four functional components of an Ugi reaction (i.e., carboxylic acid, ketone or aldehyde, isocyanide and amine) are present together, under particular reaction conditions. The reaction is referred to herein as an "Intramolecular Three Component Ugi Reaction". The three components, in fact, provide four functional components, since the ketone or aldehyde and carboxylic acid functionalities are present in the same molecule, for example, a keto-acid or an ω-carboxyaldehyde. The component wherein the aldehyde or ketone and the carboxylic acid functionalities are present in the same molecule is also referred to herein as "the difunctional component".

Thus, this invention provides an efficient and facile method for the preparation of lactams which bear a substituent(s) on the two position of the lactam ring and/or on the amide nitrogen of the ring and/or on any of the remaining carbon atoms of the lactam ring. The substitution can be a monosubstitution or a disubstitution, as appropriate, with the reactants dictating the substituents present on the final lactam. The lactams have a ring size from about four to about eight or more members. In a preferred embodiment, the lactams have a ring size of either seven or eight.

One embodiment of the present invention is a method of preparing a lactam represented by the following structural formula:

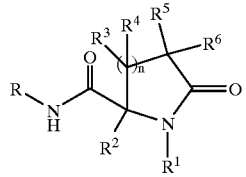

The method comprises reacting a difunctional component, $R^2$—CO—$(CR^3R^4)_n$—$(CR^5R^6)$—$CO_2H$, an amine such as ammonia or a primary amine, $R^1$—$NH_2$, and an isocyanide, R—N≡C, in a nucleophilic polar protic solvent at a concentration of the reactants suitable to form said lactam. The variable, n, can be zero or an integer of one or more. R, $R^1$, $R^2$, $R^3$, $R^4$, $R^5$ and $R^6$ can be selected according to the product(s) desired. The amine or ammonia is capable of forming an imine.

For example, R, $R^1$ and $R^2$ can, independently, be H; substituted, unsubstituted, branched, straight chain, cyclic, saturated or unsaturated alkyl, such as, methyl, ethyl, propyl, butyl, hexyl, octyl, decyl, dodecyl, isopropyl, sec-butyl, tert-butyl, isoamyl, cyclopropyl, cyclobutyl, cyclopentyl, and cyclohexyl; substituted or unsubstituted aryl, such as phenyl, naphthyl, tetrahydronaphthyl, biphenyl, phenylalkylphenyl, phenylalkenylphenyl; and heterocyclic rings, such as aromatic heterocyclic rings including, pyridinyl, pyrimidinyl, quinolinyl, thiophenyl, furanyl, pyrazolyl, imidazolyl, pyrrolyl and thiazolyl and non-aromatic heterocyclic rings, such as morpholinyl and piperidinyl, tetrahydrofuran, tetrahydropyran, and dioxane.

Optional substituents for the above include, for example, alkyl, alkoxy, hydroxy, aryl, aryloxy, aryloxycarbonyl, alkylamino, dialkylamino, amino, alkylthio, mercapto, halogen, nitro, cyano, carboxy, alkoxy carbonyl, acyloxy, aminocarbonyl, N-alkylamido, N,N-dialkylamido, acylamino, arylalkyl, sulfonic acid, sulfonic acid esters, isonitrilo and heterocyclic rings, as above.

For example, $R^3$, $R^4$, $R^5$ and $R^6$ can, independently, be H, alkoxy, hydroxy, aryloxy, aryloxycarbonyl, alkylamino, dialkylamino, amino, alkylthio, mercapto, halogen, nitro, cyano, carboxy, alkoxy carbonyl, acyloxy, aminocarbonyl, N-alkylamido, N,N-dialkylamido, acylamino, arylalkyl, sulfonic acid, sulfonic acid esters, isonitrilo; substituted, unsubstituted, branched, straight chain, cyclic, saturated or unsaturated alkyl, such as, methyl, ethyl, propyl, butyl, hexyl, octyl, decyl, dodecyl, isopropyl, sec-butyl, tert-butyl, isoamyl, cyclopropyl, cyclobutyl, cyclopentyl, and cyclohexyl; substituted or unsubstituted aryl, such as phenyl, naphthyl, tetrahydronaphthyl, biphenyl, phenylalkylphenyl, phenylalkenylphenyl; and heterocyclic rings, such as aromatic heterocyclic rings including, pyridinyl, pyrimidinyl, quinolinyl, thiophenyl, furanyl, pyrazolyl, imidazolyl, pyrrolyl and thiazolyl and non-aromatic heterocyclic rings, such as morpholinyl and piperidinyl, tetrahydrofuran, tetrahydropyran, and dioxane. At each additional position on the ring, $R^3$ and $R^4$ are again each independently selected. In addition, any of two or more of $R^3$, $R^4$, $R^5$ and $R^6$ can be taken together to form a carbocyclic or heterocyclic ring.

The difunctional components of the invention can be substituted or unsubstituted keto-acids or ω-carboxyaldehydes. Keto-acids and ω-carboxyaldehydes suitable for use in the method of the invention include those in which the carbonyl carbon of the ketone or aldehyde, also referred to as the "activated carbon", and the carbonyl carbon of the carboxylic acid are separated by from about one to about five carbon atoms. Generally, the substituent(s) of the difunctional component do not substantially interfere or compete with formation of the lactam. The substituents of the difunctional components can be present on the carbon chain which tethers the carbonyls of the difunctional component (e.g., $R^3$, $R^4$, $R^5$ and $R^6$) and/or as the substituent $R^2$. The difunctional component can be selected according to the substituents, for example, $R^2$, desired in the final product. When an aldehyde functionality is present in the difunctional component which comprises the activated carbon, $R^2$ will be hydrogen. Based on the proposed mechanism for the formation of the substituted lactams according to the invention, suitable difunctional components can be selected. Examples of the substituent(s) (e.g., $R^2$, $R^3$, $R^4$, $R^5$ and $R^6$) comprised by the difunctional component are described above.

Amines suitable for use in the method include those which are capable of forming an imine with the activated carbon of the difunctional component. Primary amines are preferred. In addition, the amine can be selected according to the substituent, $R^1$, which is desired in the final product. Generally, $R^1$ does not bear a substituent(s) which substantially interferes or competes with formation of the lactam. Based on the proposed mechanism for the formation of the lactams according to the invention, suitable amines can be selected. If ammonia is used as the amine reactant in the method, the $R^1$ substituent will be hydrogen. Examples of suitable substituents ($R^1$) comprised by the amine are described above.

Isocyanides suitable for use in the method include those selected according to the substitutent, R, which is desired in the final product(s). Generally, R does not bear a substituent which substantially interferes or competes with lactam formation. Based on the proposed mechanism for the formation of the substituted lactams according to the invention, as described herein, suitable isocyanides can be selected. Examples of suitable substituents comprised by the isocyanide are described above.

Suitable solvents include nucleophilic polar protic solvents, and are selected such that they are capable of nucleophilic addition to the acyl center of the cyclic intermediate III, as depicted in the proposed reaction mechanism contained herein. The nucleophilic attack by the solvent results in ring opening of the cyclic intermediate III. The non-cyclic intermediate then recyclizes causing the nucleophile, provided by the solvent, to leave and be regenerated as solvent. Preferably, the solvent functions as a good leaving group during this recyclization thereby facilitating the cyclization. In addition, the solvent is in the substantial absence of cosolvents which are non-nucleophilic and/or aprotic. Suitable solvents include, but are not limited to, methanol and ethanol and combinations thereof. Methanol is the preferred solvent, and preferably is present in substantial excess of the reactants and/or intermediates, for example, intermediate III.

The components used in the method of the invention should be maintained at a concentration suitable to promote the intramolecular cyclization necessary to form the substituted lactams described herein. Preferably, the reactants are present in a dilute concentration relative to the nucleophilic polar protic solvent. A range of concentration suitable for each reactant employed in the method of the invention can be from about 0.01 to about 1M. The reactants (i.e., the difunctional component, amine and isocyanide) can be present in equimolar amounts or any one or two in excess of the remaining reactant(s). Preferably, the amine is present in excess of each of the isocyanide and the difunctional component. It will be appreciated that the characteristics of the solvent and the nature of the reactants being employed, need to be considered in determining a suitable concentration.

The temperature is not generally critical to product formation. The reaction is preferably conducted in solution. Thus, a reaction temperature ranging from between the freezing point and the boiling point of the solvent employed is generally suitable. For example, if methanol is the reaction solvent, a reaction temperature ranging from between −98° C. to 64.7° C. is acceptable. More preferably, the temperature is between about 15° C. to about 50° C. In a particular embodiment, approximated room temperature (RT) or ambient temperature, is preferred. The system can be opened or closed, and the reaction can be conducted in either the presence or absence of an inert atmosphere.

Following completion of the reaction, the reaction mixture can be worked up using conventional methods to provide the product(s) in an acceptable purity or in a form which can be further purified. For example, salt solutions, acid solutions, basic solution and/or organic solvents can be employed to extract impurities and/or unreacted starting materials from the crude reaction mixture. Solvent evaporation and/or distillation are other techniques which can also be employed in working up the reaction. Further purification of the substituted lactams of the invention can include methods such as chromatography, distillation and solvent recrystallization, or other suitable methods.

According to the proposed reaction mechanism depicted below, the number of carbon atoms which separates the activated carbon of the difunctional component from the carbonyl carbon of the carboxylic acid in the difunctional component, is determinative of the size of the lactam ring obtained according to the method of the invention. For example, when a keto-acid or ω-carboxyaldehyde having one, two, three, four or five carbon atoms between the activated carbon and the carbonyl carbon of the acid is employed, the resulting lactam will have a ring size of four, five, six, seven or eight members, respectively. The method is particularly preferred for the synthesis of seven and eight membered lactam rings.

Without being bound to any particular theory, the reaction proceeds first through the formation of imine I. Subsequent addition of the isocyanide results in the formation of nitrilium intermediate II. Intramolecular attack of the carboxylate on the nitrilium carbon results in cyclic intermediate III. Addition of a suitable solvent such as methanol, to the acyl center results in ring opening which is then quickly followed by lactam formation (Product IV).

The lactams prepared by the method of the invention can be represented by the following structural formula:

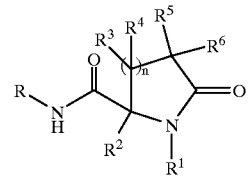

The lactams are 2,2-disubstituted when a keto-acid is employed as the difunctional component. Alternatively, the lactams can be monosubstituted at the two position of the lactam ring if an aldehyde functionality is present, rather than a ketone functionality in the difunctional component. The 2,2-disubstituted lactams are preferred. The ring size of the lactams can be from about four to about eight members. The five, six, seven and eight membered lactam rings are commonly referred to as pyrrolidinones, piperidinones, azepinones and azocanones, respectively. In certain embodiments, the amide nitrogen of the lactam ring is also substituted, with the substituent being introduced by the amine component of the reaction, and/or the remaining carbons on the lactam ring are substituted with the substituent(s) being introduced by the difunctional component. Lactams having a ring size which includes seven or eight members are preferred.

The compounds of the invention can be useful, for example, as antibiotics, modulators of cholesterol absorption (See for example, Dugar, S., et al., *Bio. Med. Chem.*

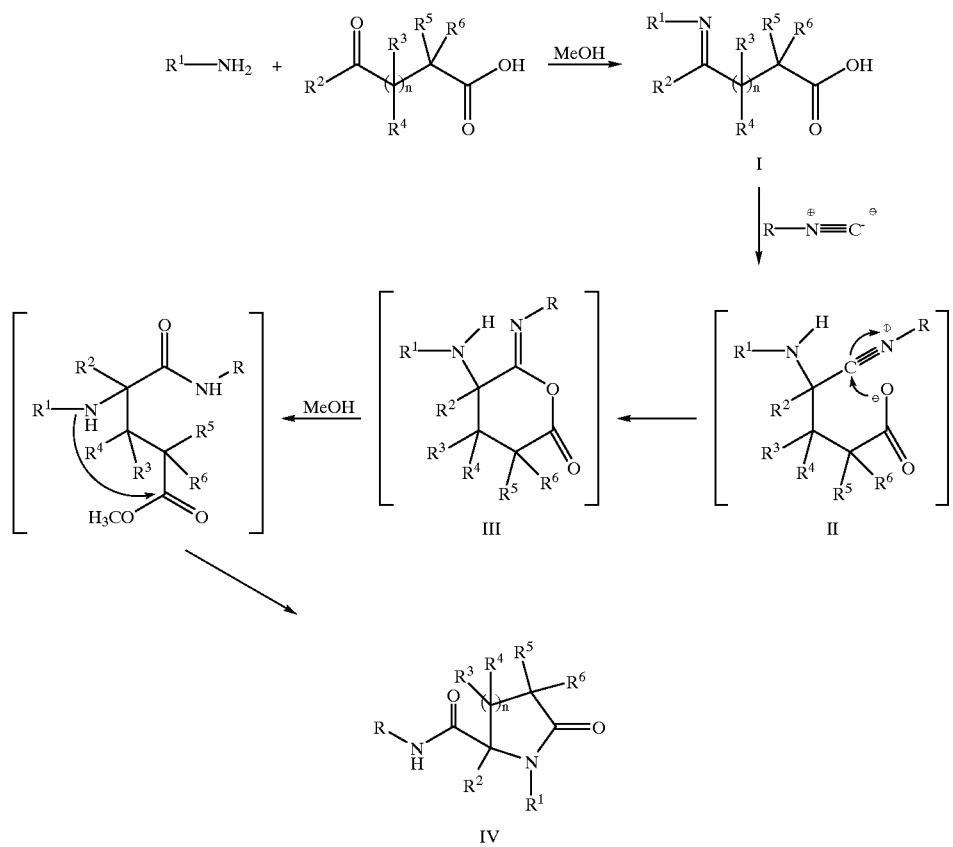

Lett., 5: 2947 (1995)), analgesics (See for example, Napoletano, M., et al., Bio. Med. Chem Lett., 5: 589 (1995)) and bronchodilators (See for example, European Patent EP 404737 to DeAngeli). Further, the lactams of the invention, in view of their peptidic nature, can be used as conformationally constrained mimics of peptides or peptide derivatives, which can be used for a variety or purposes, including the elucidation of the preferred conformation which a particular peptide adopts when bound to a specific receptor (See for example, Garvey, D., et al., J. Org. Chem, 55: 936–940 (1990) and Kemp, D., et al., J. Org. Chem., 50: 5834–5838 (1985)) or as peptide-like compounds designed to mimic a natural polypeptide or portion thereof.

Importantly, the facile nature and one vessel methodology of the invention allows for the efficient synthesis of a diverse collection of lactams useful in, for example, a combinatorial library for screening for compounds having a desired property, for example, in the discovery of new drugs. Therefore, another aspect of the invention relates to a method for generating a library of compounds, having the following structural formula:

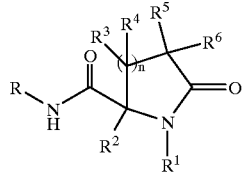

comprising reacting a difunctional component, $R^2$—CO—$(CR^3R^4)_n$—$(CR^5R^6)$—$CO_2H$, an amine, $R^1$—$NH_2$, and an isocyanide, R—N≡C, in a nucleophilic polar protic solvent at a concentration of the reactants suitable to form said lactam. The variable, n, can be zero or an integer of one or more. R, $R^1$, $R^2$, $R^3$, $R^4$, $R^5$, and $R^6$ can be selected according to the substituents described above and the product desired.

In an additional embodiment, the invention relates to a library of compounds prepared according to the method of the invention, comprising a plurality of compounds represented by the following structural formula:

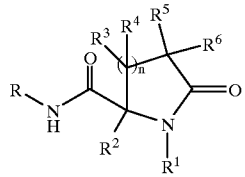

The variable, n, can be zero or an integer of one or more. R, $R^1$, $R^2$, $R^3$, $R^4$, $R^5$, and $R^6$ can be selected according to the substituents described above and the product desired.

The data contained in the Table below in conjunction with the reaction mechanism depicted above, provide some examples of compounds synthesized by the method of the invention. Further details of the synthesis are provided in the Examples.

TABLE

Lactams Prepared via the Three Component Intramolecular Ugi Reaction

| Example | n | $R^1$—$NH_2$ | $^\ominus C\!\equiv\!N^\oplus$—R | Yield |
|---|---|---|---|---|
| 1 | 1 | benzylamine | benzyl isocyanide | 62% |
| 2 | 1 | benzylamine | n-butyl isocyanide | 64% |
| 3 | 1 | benzylamine | 2-morpholinoethyl isocyanide | 61% |
| 4 | 1 | 4-(3-aminopropyl)-morpholine | benzyl isocyanide | 79% |
| 5 | 1 | 4-(3-aminopropyl)-morpholine | n-butyl isocyanide | 76% |
| 6 | 1 | 4-(3-aminopropyl)-morpholine | 2-morpholinoethyl isocyanide | 77% |
| 7 | 2 | benzylamine | benzyl isocyanide | 62% |
| 8 | 2 | benzylamine | n-butyl isocyanide | 58% |
| 9 | 2 | benzylamine | 2-morpholinoethyl isocyanide | 61% |
| 10 | 2 | isoamylamine | benzyl isocyanide | 54% |
| 11 | 2 | 4-(3-aminopropyl)-morpholine | benzyl isocyanide | 60% |
| 12 | 2 | 4-(3-aminopropyl)-morpholine | butyl isocyanide | 56% |
| 13 | 2 | 4-(3-aminopropyl)-morpholine | 2-morpholinoethyl isocyanide | 50% |
| 14 | 3 | benzylamine | benzyl isocyanide | 23% |
| 15 | 3 | isoamyl amine | benzyl isocyanide | 27% |
| 16 | 3 | 4-(3-aminopropyl)-morpholine | benzyl isocyanide | 44% |
| 17 | 4 | 4-(3-aminopropyl)-morpholine | n-butyl | 41% |
| 18 | 4 | benzylamine | benzyl isocyanide | 65% |

EXEMPLIFICATION

Spectra were obtained as follows: FAB or ESI mass spectra were performed by M-Scan, Westchester, Pa. using either a VG-Analytical ZAB 2-SE or VG Biotech Bio-Q; Microanalyses were performed by Galbraith Laboratories, Inc., Knoxville, Tenn.

The invention will now be further illustrated by the following examples which are not intended to limit the scope of the invention in any way.

EXAMPLE 1

To a stirred solution of levulinic acid (5 mmol) in methanol (25 mL) at room temperature (RT) was added benzylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 62%. $M^+$ 323

EXAMPLE 2

To a stirred solution of levulinic acid (5 mmol) in methanol (25 mL) at room temperature was added benzylamine (6.25 mmol) at once. The reaction was stirred at RT for 45 minutes to ensure imine formation. Butyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 64%. $M^+$ 289

EXAMPLE 3

To a stirred solution of levulinic acid (5 mmol) in methanol (25 mL) at room temperature was added benzylamine (6.25 mmol) at once. The reaction was stirred at RT for 45 minutes to ensure imine formation. 2-morpholinoethyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 61%. $M^+$ 346.

EXAMPLE 4

To a stirred solution of levulinic acid (5 mmol) in methanol (25 mL) at room temperature was added 4-(3-aminopropyl)morpholine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved into 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 79%. $M^+$ 360.

EXAMPLE 5

To a stirred solution of levulinic acid (5 mmol) in methanol (25 mL) at room temperature was added 4-(3-aminopropyl)morpholine (6.25 mol) at once. The reaction was stirred at RT for 45 minutes to ensure imine formation. Butyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 76%. $M^+$ 326

EXAMPLE 6

To a stirred solution of levulinic acid (5 mmol) in methanol (25 mL) at room temperature was added 4-(3-aminopropyl)morpholine (6.25 mmol) at once. The reaction was stirred at RT for 45 minutes to ensure imine formation. 2-morpholinoethyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 77%. $M^+$ 383

EXAMPLE 7

To a stirred solution of 4-acetylbutyric acid (5 mmol) in methanol (25 mL) at room temperature was added benzylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 62%. $M^+$ 337

EXAMPLE 8

To a stirred solution of 4-acetylbutyric acid (5 mmol) in methanol (25 mL) at room temperature was added benzylamine (6.25 mmol) at once. The reaction was stirred at RT for 45 minutes to ensure imine formation. Butyl isocyanide (5 mmol) was added at once and the reaction was stirred at room temperature for 48 hrs. Excess methanol was removed under reduced pressure and the reaction residue was brought up into 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 58%. $M^+$ 303

EXAMPLE 9

To a stirred solution of 4-acetylbutyric acid (5 mmol) in methanol (25 mL) at room temperature was added benzylamine (6.25 mmol) at once. The reaction was stirred at RT for 45 minutes to ensure imine formation. 2-morpholinoethyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 61%. $M^+$ 360

EXAMPLE 10

To a stirred solution of 4-acetylbutyric acid (5 mmol) in methanol (25 mL) at room temperature was added isoamylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was brought up into 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 54%. $M^+$ 317

EXAMPLE 11

To a stirred solution of 4-acetylbutyric acid (5 mmol) in methanol (25 mL) at room temperature was added 4-(3-aminopropyl)morpholine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 60%. $M^+$ 374

EXAMPLE 12

To a stirred solution of 4-acetylbutyric acid (5 mmol) in methanol (25 mL) at room temperature was added 4-(3-aminopropyl)morpholine (6.25 mmol) at once. The reaction was stirred at RT for 45 minutes to ensure imine formation. butyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 56%. $M^+$ 340

EXAMPLE 13

To a stirred solution of 4-acetylbutyric acid (5 mmol) in methanol (25 mL) at room temperature was added 4-(3-aminopropyl)morpholine (6.25 mmol) at once. The reaction was stirred at RT for 45 minutes to ensure imine formation. 2-morpholinoethyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 50%. $M^+$ 397

EXAMPLE 14

To a stirred solution of 6-oxoheptanoic acid (5 mmol) in methanol (25 mL) at room temperature was added benzylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 23%. CHN analysis within 0.4% theoretical:$C_{22}H_{26}NO_2 \cdot 0.9CH_3OH$, 73.04% C, 8.09% H, 7.13% N.

EXAMPLE 15

To a stirred solution of 6-oxoheptanoic acid (5 mmol) in methanol (25 mL) at room temperature was added isoamylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (in most cases from 20% hexanes/$CH_2Cl_2$). The yield of product was 27%. $M^+$ 331

EXAMPLE 16

To a stirred solution of 6-oxoheptanoic acid (5 mmol) in methanol (25 mL) at room temperature was added 4-(3-aminopropyl)morpholine (6.25 mmol) at once. The reaction was stirred at RT for 45 minutes to ensure imine formation. Butyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 44%. $M^+$ 317

EXAMPLE 17

To a stirred solution of 7-oxooctanoic acid (5 mmol) in methanol (25 mL) at room temperature was added 4-(3-aminopropyl)morpholine (6.25 mmol) at once. The reaction was stirred at RT for 45 minutes to ensure imine formation. Butyl isocyanide (5 mmol) was added at once and the reaction was stirred at room temperature for 48 hrs. Excess methanol was removed under reduced pressure and the reaction residue was redissolved in 50 mL of $CH_2Cl_2$.

The organic layer was extracted with 10% HCl (aq). The acidic aqueous layer was separated and subsequently neutralized by the slow careful addition of solid KOH to afford a solution pH of 13. The product was then extracted from the water layer with ethyl acetate. The organic layer containing the product was dried over $Na_2SO_4$. The solvent was removed under reduced pressure and the resulting product was recrystallized. The yield of product was 41%. $M^+$ 368

EXAMPLE 18

To a stirred solution of 7-oxooctanoic acid (5 mmol) in methanol (25 mL) at room temperature was added benzylamine (6.25 mmol) at once. The reaction was stirred at RT for 45 minutes to ensure imine formation. Benzyl isocyanide (5 mmol) was added at once and the reaction was stirred at room temperature for 48 hrs. Excess methanol was removed under reduced pressure and the reaction residue was redissolved in 50 mL of $CH_2Cl_2$.

The mixture was washed with 10% (aq) HCl (50 mL) which ensures removal of the starting amine. The organic layer was separated and washed with 6 M NaOH (aq) (50 mL) which ensures the removal of the starting keto-acid. The organic layer was dried over $Na_2SO_4$, and the solvent was removed. Pure lactam was recrystallized (20% hexanes/$CH_2Cl_2$). The yield of product was 65%. CHN analysis within 0.4% theoretical: $C_{23}H_{29}N_2O_2 \cdot CH_3OH$, 72.22% C, 7.32% H, 7.91% N.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of preparing a compound represented by the following structural formula:

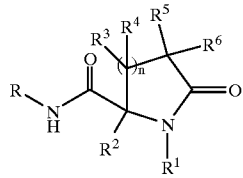

comprising reacting a difunctional component, $R^2$—CO—$(CR^3R^4)_n$—$(CR^5R^6)$—$CO_2H$, an amine $R^1$—$NH_2$, and an isocyanide, R—N=C, in the presence of a nucleophilic polar protic solvent, wherein n can be zero or an integer of one or more; and R, $R^1$, and $R^2$ are independently selected from the group consisting of: H, substituted or unsubstituted alkyl, substituted or unsubstituted aryl and heterocyclic rings; and $R^3$, $R^4$, $R^5$ and $R^6$ are independently selected from the group consisting of: H, substituted or unsubstituted alkyl, alkoxy, hydroxy, aryl, aryloxy, aryloxycarbonyl, alkylamino, dialkylamino, amino, alkylthio, mercapto, halogen, nitro, cyano, carboxy, alkoxy carbonyl, acyloxy, aminocarbonyl, N-alkylamido, N,N-dialkylamido, acylamino, arylalkyl, sulfonic acid, sulfonic acid esters, isonitrilo, substituted or unsubstituted aryl and heterocyclic rings.

2. The method of claim 1 wherein the nucleophilic polar protic solvent is methanol, ethanol or a mixture thereof.

3. The method of claim 1 wherein the difunctional component is a keto-acid.

4. The method of claim 1 wherein the difunctional component is an ω-carboxyaldehyde.

5. The method of claim 3 wherein n is one.

6. The method of claim 3 wherein n is two.

7. The method of claim 3 wherein n is three.

8. The method of claim 3 wherein n is four.

9. A method of preparing a compound represented by the following structural formula:

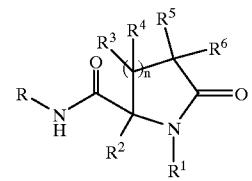

comprising reacting a difunctional component, $R^2$—CO—$(CR^3R^4)_n$—$(CR^5R^6)$—$CO_2H$, an amine $R^1$—$NH_2$, and an isocyanide, R—N=C, in the presence of a nucleophilic polar protic solvent which is in the substantial absence of a non-nucleophilic and/or aprotic solvent, wherein n can be zero or an integer of one or more; and R, $R^1$, and $R^2$ are independently selected from the group consisting of: H, substituted or unsubstituted alkyl, substituted or unsubstituted aryl and heterocyclic rings; and $R^3$, $R^4$, $R^5$ and $R^6$ are independently selected from the group consisting of: H, substituted or unsubstituted alkyl, alkoxy, hydroxy, aryl, aryloxy, aryloxycarbonyl, alkylamino, dialkylamino, amino, alkylthio, mercapto, halogen, nitro, cyano, carboxy, alkoxy carbonyl, acyloxy, aminocarbonyl, N-alkylamido, N,N-dialkylamido, acylamino, arylalkyl, sulfonic acid, sulfonic acid esters, isonitrilo, substituted or unsubstituted aryl and heterocyclic rings.

10. The method of claim 9 wherein the nucleophilic polar protic solvent is methanol, ethanol or a mixture thereof.

11. The method of claim 9 wherein the difunctional component is a keto-acid.

12. The method of claim 9 wherein the difunctional component is an ω-carboxyaldehyde.

13. The method of claim 9 wherein n is one.

14. The method of claim 9 wherein n is two.

15. The method of claim 9 wherein n is three.

16. The method of claim 9 wherein n is four.

* * * * *

UNITED STATES PATENT AND TRADEMARK OFFICE
CERTIFICATE OF CORRECTION

PATENT NO.   : 6,054,579
DATED        : April 25, 2000
INVENTOR(S)  : Geraldine C.B. Harriman Page 1 of 1

It is certified that error appears in the above-identified patent and that said Letters Patent is hereby corrected as shown below:

Column 2,
Line 65, delete "R-N=C" and insert -- R-N≡C --.

Column 7,
Line 37, delete "R-N=C" and insert -- R-N≡C --.

Column 13,
Line 54, delete "R-N=C" and insert -- R-N≡C --.

Column 14,
Line 33, delete "R-N=C" and insert -- R-N≡C --.

Signed and Sealed this

Seventh Day of January, 2003

JAMES E. ROGAN
*Director of the United States Patent and Trademark Office*